US011110188B2

(12) United States Patent
Matsumura et al.

(10) Patent No.: US 11,110,188 B2
(45) Date of Patent: Sep. 7, 2021

(54) ELECTRON BEAM IRRADIATION DEVICE

(71) Applicant: HAMAMATSU PHOTONICS K.K., Hamamatsu (JP)

(72) Inventors: Tatsuya Matsumura, Hamamatsu (JP); Takeaki Hattori, Hamamatsu (JP); Keigo Uchiyama, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 342 days.

(21) Appl. No.: 16/338,785

(22) PCT Filed: Jul. 3, 2017

(86) PCT No.: PCT/JP2017/024393
§ 371 (c)(1),
(2) Date: Apr. 2, 2019

(87) PCT Pub. No.: WO2018/078953
PCT Pub. Date: May 3, 2018

(65) Prior Publication Data
US 2021/0113722 A1    Apr. 22, 2021

(30) Foreign Application Priority Data

Oct. 26, 2016  (JP) .............................. JP2016-209675

(51) Int. Cl.
*A61L 2/08*       (2006.01)
*H01J 33/04*    (2006.01)
*B65B 55/08*    (2006.01)

(52) U.S. Cl.
CPC .............. *A61L 2/087* (2013.01); *B65B 55/08* (2013.01); *H01J 33/04* (2013.01); *A61L 2202/23* (2013.01)

(58) Field of Classification Search
CPC ........ A61L 2202/23; A61L 2/087; A61L 2/26; G21K 5/04; G21K 5/00; H01J 33/00; H01J 33/04
(Continued)

(56) References Cited

U.S. PATENT DOCUMENTS 8,294,126 B2 * 10/2012 Humele .................. H01J 33/00
                                                          250/492.3
9,434,495 B2 *  9/2016 Yokobayashi ............ A61L 2/26
(Continued)

FOREIGN PATENT DOCUMENTS

CN        104619109 A     5/2015
EP          1982920 A1   10/2008
(Continued)

OTHER PUBLICATIONS

International Preliminary Report on Patentability dated May 9, 2019 for PCT/JP2017/024393.

*Primary Examiner* — David A Vanore
(74) *Attorney, Agent, or Firm* — Faegre Drinker Biddle & Reath LLP

(57) ABSTRACT

An electron beam irradiation device includes an electron gun, a housing, and an electron beam emission window. A rod portion of the housing includes a first tubular member, a second tubular member, a cooling gas flow space, and a wall member. The window is provided at an end portion on a distal end side of the first tubular member. The second tubular member surrounds the first tubular member. The cooling gas flow space includes at least a cooling gas flow path provided between an outer wall surface of the first tubular member and an inner wall surface of the second tubular member. The wall member is provided so as to perform partition between an electron beam emission space and the cooling gas flow space. The wall member is provided (Continued)

with a cooling gas ejection hole. The hole has a flow path sectional area smaller than a flow path sectional area of the cooling gas flow path.

9 Claims, 10 Drawing Sheets

(58) Field of Classification Search
USPC .................. 422/22; 250/491.1, 492.1, 492.3
See application file for complete search history.

(56) References Cited

U.S. PATENT DOCUMENTS

| | | | | |
|---|---|---|---|---|
| 9,601,224 | B2* | 3/2017 | Sakai | ................. G21K 5/04 |
| 10,398,794 | B2* | 9/2019 | Daiku | ................. B65B 55/08 |
| 2008/0073549 | A1* | 3/2008 | Avnery | ................. G21K 5/04 |
| | | | | 250/397 |
| 2011/0076187 | A1* | 3/2011 | Foell | ................. H01J 33/04 |
| | | | | 422/22 |
| 2016/0064111 | A1* | 3/2016 | Sakai | ................. G21K 5/00 |
| | | | | 250/496.1 |

FOREIGN PATENT DOCUMENTS

| | | | |
|---|---|---|---|
| GB | | 277347 A | 12/1928 |
| JP | | S49-41799 A | 4/1974 |
| JP | | H11-38196 A | 2/1999 |
| JP | | 2001-13300 A | 1/2001 |
| JP | | 2004-361096 A | 12/2004 |
| JP | | 2009-068973 A | 4/2009 |
| JP | | 5753047 B2 | 7/2015 |
| WO | WO 2007/145561 | A1 | 12/2007 |
| WO | WO-2014/175065 | A1 | 10/2014 |
| WO | WO-2015/125414 | A1 | 8/2015 |

* cited by examiner

ELECTRON BEAM IRRADIATION DEVICE

TECHNICAL FIELD

One aspect of the present invention relates to an electron beam irradiation device.

BACKGROUND ART

Conventionally, there has been known an electron beam irradiation device which includes: an electron gun emitting an electron beam; a housing that has a main body portion housing the electron gun and a rod portion protruding from the main body portion; and an electron beam emission window provided on a distal end side of the rod portion (for example, see Patent Literatures 1 and 2).

In a device described in Patent Literature 1, a nozzle member (rod portion) has a double tube structure formed of an inner nozzle tubular body and an outer nozzle tubular body. A rise in temperature in the vicinity of an emission window (electron beam emission window) of the nozzle member is suppressed by supplying cooling water between the inner nozzle tubular body and the outer nozzle tubular body. In a device described in Patent Literature 2, a processing head (rod portion) is formed as a double wall having an outer housing and an inner housing. A gas flowing along a gap between the outer housing and the inner housing is guided so as to pass through an emission side of an emission window (electron beam emission window), thereby cooling the emission window.

CITATION LIST

Patent Literature

Patent Literature 1: WO 2014/175065
Patent Literature 2: Japanese Patent No. 5753047

SUMMARY OF INVENTION

Technical Problem

In the above electron beam irradiation device, for example, the rod portion is extended so as to protrude from the main body portion in order to insert the rod portion into a container to directly irradiate the inside of a container with electron beams. Even in this case, heat generation at the electron beam emission window is one of major problems, and efficient cooling of the electron beam emission window is required. The electron beam emission window is provided on the distal end side of the extending rod portion, and thus, is arranged at a position away from the main body portion. For this reason, it is difficult to expect an effect of cooling the electron beam emission window with heat dissipation or cooling using the main body portion, and it is desirable to provide a cooling structure directly in the rod portion provided with the electron beam emission window.

In the device described in Patent Literature 1, the electron beam emission window is not cooled directly but cooled indirectly by cooling the vicinity of the electron beam emission window of the rod portion. Thus, there is a risk that it is difficult to efficiently cool the electron beam emission window.

In the case of direct cooling of the electron beam emission window, it is conceivable to cool the electron beam irradiation window by bringing a cooling gas into contact with the electron beam emission window. In this case, it is preferable to increase pressure (dynamic pressure) of the cooling gas to be brought into contact in order to efficiently cool the electron beam emission window. In the device described in Patent Literature 2, however, the fact of raising the pressure of the cooling gas is not sufficiently considered so that there is a risk that the cooling efficiency of the electron beam emission window is not sufficient.

Therefore, one aspect of the present invention is to provide an electron beam irradiation device capable of efficiently cooling an electron beam emission window provided on a distal end side of an extending rod portion.

Solution to Problem

An electron beam irradiation device according to one aspect of the present invention includes: an electron gun configured to emit an electron beam; a housing configured to have a main body portion housing the electron gun and a rod portion having a proximal end side connected to the main body portion and a distal end side protruding from the main body portion; and an electron beam emission window provided on the distal end side of the rod portion. The rod portion includes: a first tubular member which has a tubular shape with an extending direction of the rod portion as an axial direction, is provided with the electron beam emission window at an end portion on the distal end side, and has an inside through which the electron beam passes; a second tubular member which has a tubular shape with the extending direction of the rod portion as an axial direction and surrounds the first tubular member; a cooling gas flow space for a cooling gas introduced from the proximal end side to flow to the distal end side, and including at least a cooling gas flow path provided between an outer wall surface of the first tubular member and an inner wall surface of the second tubular member; and a wall member provided so as to perform partition between an electron beam emission space facing an electron beam emission side of the electron beam emission window and the cooling gas flow space. The wall member is provided with a cooling gas ejection hole that ejects the cooling gas from the cooling gas flow space to the electron beam emission space. The cooling gas ejection hole has a flow path sectional area smaller than a flow path sectional area of the cooling gas flow path.

In this electron beam irradiation device, the cooling gas passes through the cooling gas flow path between the outer wall surface of the first tubular member and the inner wall surface of the second tubular member, and is ejected from the cooling gas ejection hole of the wall member to the electron beam emission space. As a result, the cooling air is brought into contact with the electron beam emission window on the distal end side of the extending rod portion, and can directly cool the electron beam emission window. At this time, since the cooling gas ejection hole has the flow path sectional area smaller than the flow path sectional area of the cooling gas flow path, it is possible to increase the pressure of the cooling gas to be ejected. That is, it becomes possible to directly supply the cooling gas with high pressure to the electron beam emission window. Therefore, it is possible to efficiently cool the electron beam emission window provided on the distal end side of the extending rod portion.

In the electron beam irradiation device according to one aspect of the present invention, the cooling gas ejection hole may eject the cooling gas toward an electron beam emission region of the electron beam emission window. As a result, the cooling gas can be directly blown to a part of the electron beam emission window where the temperature is the highest, whereby it is possible to more efficiently cool the electron beam emission window.

In the electron beam irradiation device according to one aspect of the present invention, a plurality of the cooling gas ejection holes may be provided in the wall member, and the cooling gas flow space may further include distal end space formed around the wall member and causing the cooling gas flow path to communicate with the plurality of cooling gas ejection holes. In this case, the supply of the cooling gas to the plurality of cooling gas ejection holes is performed from the common distal end space. As a result, it is possible to make states of cooling gases ejected, respectively, from the plurality of cooling gas ejection holes uniform. It is possible to efficiently perform cooling with less deviation with respect to the electron beam emission window.

In the electron beam irradiation device according to one aspect of the present invention, the cooling gas flow space may include a plurality of the cooling gas flow paths, and further include a proximal end space which is formed on the proximal end side of the rod portion and communicates with the plurality of cooling gas flow paths, and into which the cooling gas is introduced from an outside the rod portion. In this case, the cooling gas is supplied to the plurality of cooling gas flow paths from the common proximal end space. As a result, it is possible to make states of cooling gases flowing, respectively, through the plurality of cooling gas flow paths uniform. It is possible to efficiently perform cooling with less deviation with respect to the electron beam emission window.

In the electron beam irradiation device according to one aspect of the present invention, at least one of the outer wall surface of the first tubular member and the inner wall surface of the second tubular member may be formed with a separating portion separating the outer wall surface from the inner wall surface so as to form the cooling gas flow path, in a cross section perpendicular to the extending direction of the rod portion, and the outer wall surface of the first tubular member and the inner wall surface of the second tubular member may be in contact with each other at at least two points in the cross section perpendicular to the extending direction of the rod portion. Since the outer wall surface of the first tubular member and the inner wall surface of the second tubular member are in contact with each other at at least two points, it is possible to maintain the cooling gas flow path with high accuracy even when a force to change a distance between the first tubular member and the second tubular member is applied due to an external factor or the like during an operation, for example. It is possible to stably cause the cooling gas to flow through the cooling gas flow path. As a result, it is possible to stably cool the electron beam emission window.

In the electron beam irradiation device according to one aspect of the present invention, the separating portion may be formed on the outer wall surface of the first tubular member. In this case, it is possible to easily form the separating portion.

The electron beam irradiation device according to one aspect of the present invention may include an adjustment unit configured to adjust an orbit of the electron beam and a converging unit configured to control converging of the electron beam. As the orbit and the converging of the electron beam are appropriately adjusted, it is possible to prevent the electron beam from being incident on the inner wall surface of the first tubular member, and to efficiently guide the electron beam to the electron beam emission window. As a result, it is possible to suppress heat generation of the rod portion. It is possible to prevent the cooling gas flowing through the cooling gas flow path from being heated by the heat generation. As a result, it is possible to suppress a temperature rise of the cooling gas reaching the electron beam emission window due to the heating. It is possible to more efficiently cool the electron beam emission window.

In the electron beam irradiation device according to one aspect of the present invention, at least one of the first tubular member and the second tubular member may be made of a magnetic material. As a result, it is possible to suppress influence of an external magnetic field onto the electron beam passing through the inside of the first tubular member.

In the electron beam irradiation device according to one aspect of the present invention, the electron beam emission window may be arranged on an end face of the first tubular member on the distal end side, and the wall member may have a tubular shape and be arranged on a surface of the electron beam emission window on the electron beam emission side. The electron beam irradiation device may further include a pressing member detachably fixed to the second tubular member and configured to press the wall member toward the electron beam emission window. In this case, it is possible to press and fix the electron beam emission window using the wall member provided with the cooling gas ejection hole. In addition, it is possible to easily replace the electron beam emission window by detaching the pressing member.

Advantageous Effects of Invention

According to one aspect of the present invention, it is possible to provide the electron beam irradiation device capable of efficiently cooling the electron beam emission window provided on the distal end side of the extending rod portion.

BRIEF DESCRIPTION OF DRAWINGS

FIG. 4(*b*) is a cross-sectional view taken along line B-B of FIG. 3.

FIG. 8(*b*) is an enlarged cross-sectional view illustrating a distal end side of a rod portion according to a second modification. FIG. 8(*c*) is an enlarged cross-sectional view illustrating a distal end side of a rod portion according to a third modification.

DESCRIPTION OF EMBODIMENTS

Figure 1:
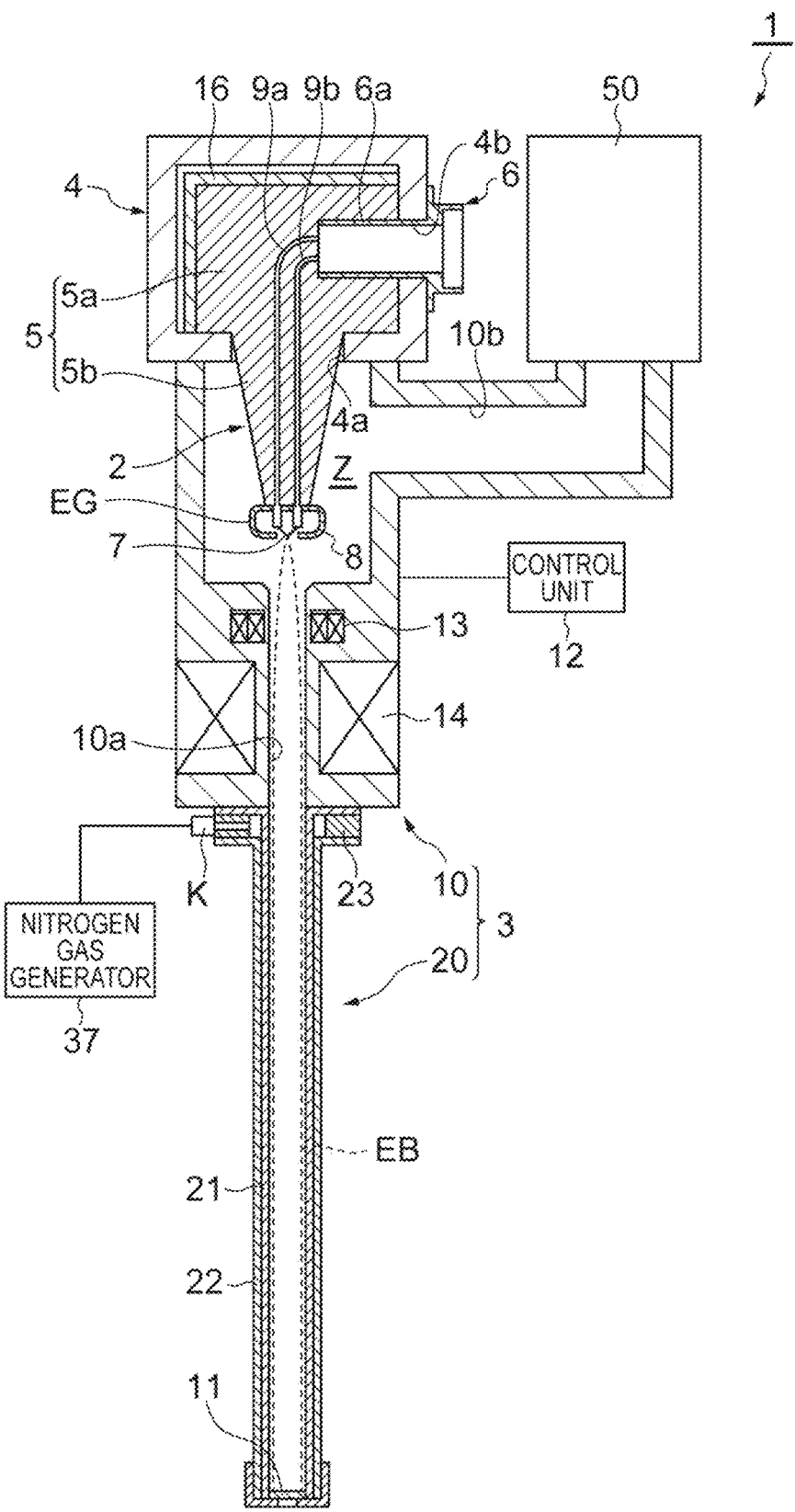
FIG. 1 is a cross-sectional view illustrating an electron beam irradiation device according to an embodiment.

Hereinafter, embodiments of the present invention will be described in detail while referring to the drawings. In the following description, the same or equivalent elements will be denoted by the same reference signs, and redundant descriptions thereof will be omitted.

FIG. 1 is a cross-sectional view of an electron beam irradiation device 1 according to one embodiment. The electron beam irradiation device 1 illustrated in FIG. 1 is used to perform sterilization, pasteurization, drying, surface modification, or the like of an irradiation target by irradiating the irradiation target with an electron beam EB. The electron beam irradiation device 1 includes an electron beam generation unit 2, a housing 3, an electron beam emission window 11, a control unit 12, an adjusting electromagnetic coil 13, and a converging electromagnetic coil 14.

The electron beam generation unit 2 includes an electron gun EG that emits the electron beam EB which is an electron beam having energy of several keV to several 100 keV, for example. The electron gun EG includes a filament 7 and a grid portion 8. The electron gun EG is housed in a vacuum space Z inside the housing 3. The electron beam generation unit 2 includes not only the electron gun EG but also a case 4, an insulating block 5, a connector 6, internal wirings 9a and 9b, and a conductive member 16.

The case 4 is made of a conductive material such as metal. The case 4 houses the insulating block 5. The case 4 has an opening 4a leading to the vacuum space Z inside the housing 3 and an opening 4b leading to the outside of the electron beam irradiation device 1a. The opening 4a is a circular opening configured to allow the internal wirings 9a and 9b to pass therethrough. The opening 4b is a circular opening configured to attach the connector 6.

The insulating block 5 is made of an insulating material. The insulating material is, for example, an insulating resin such as an epoxy resin and ceramic. The insulating block 5 insulates the internal wirings 9a and 9b from other portions (for example, the case 4 and the like). The insulating block 5 has a base portion 5a and a convex portion 5b protruding from the base portion 5a. The base portion 5a is housed in the case 4 so as to occupy most of the inside of the case 4. The convex portion 5b protrudes forward from the base portion 5a through the opening 4a and is exposed from the case 4.

The connector 6 is a high withstand voltage type connector (receptacle) configured to receive supply of a power-supply voltage of several kV to several 100 kV from the outside of the electron beam irradiation device 1a. The connector 6 is attached to a side surface of the case 4. The connector 6 is arranged in the opening 4b so as to penetrate a side wall of the case 4. A portion 6a of the connector 6 positioned inside the case 4 is embedded and fixed in the base portion 5a of the insulating block 5. The connector 6 firmly fixes the insulating block 5 and the case 4. A power supply plug holding a distal end of an external wiring, which extends from a power supply device (not illustrated), is inserted to the connector 6. Incidentally, a high voltage may be generated by boosting a voltage of several 10 V to several 100 V supplied from the outside by a boost unit enclosed in the insulating block 5, instead of supplying the high voltage of several kV to several 100 kV itself from the outside of the electron beam irradiation device 1a.

The electron gun EG is arranged on the distal end side of the convex portion 5b of the insulating block 5. The electron gun EG includes the filament 7, which is an electron emitting member that emits electrons to form the electron beam EB, and the grid portion 8 which is arranged to cover the filament 7 and extracts electrons and forms an electric field for suppressing diffusion. The filament 7 is made of a material containing tungsten as a main component. Both ends of the filament 7 are connected to the internal wirings 9a and 9b, respectively, extending from the connector 6 to the filament 7. Therefore, when the power supply plug is inserted into the connector 6, both the ends of the filament 7 are electrically connected to the power supply device via the external wiring. The filament 7 is heated to about 2,500° C. as a current of several amperes flows thereto. The filament 7 emits electrons when a high negative voltage such as minus several kV to minus several 100 kV is applied from another power supply device. A predetermined voltage is applied to the grid portion 8 via a wiring (not illustrated). Therefore, the electrons which have been emitted from the filament 7 are emitted as the electron beam EB from a hole formed in a part of the grid portion 8.

The internal wirings 9a and 9b are high-voltage portions to which a high voltage is applied from the power supply device. The internal wirings 9a and 9b are embedded in the insulating block 5 to secure insulation from the case 4.

The conductive member 16 is a conductive member that covers a surface out of a surface of the insulating block 5 where a gap is formed between the insulating block 5 and the case 4. As the conductive member 16, a thin member such as a conductive film and a conductive tape is used. The conductive member 16 is attached to the insulating block 5 so as to completely cover a portion of the insulating block 5 that is not in close contact with the case 4. The conductive member 16 may be a conductive coating material, a conductive film, or the like.

The housing 3 has a main body portion 10 and a rod portion 20. The main body portion 10 is a vacuum container constituting a vacuum space Z housing the electron gun EG. The main body portion 10 is made of a conductive material such as metal. The main body portion 10 houses and hermetically seals the electron gun EG and the convex portion 5b which is a part of the insulating block 5. A passing hole 10a is formed in a portion of the main body portion 10 opposite to the electron beam emission side of the electron gun EG. The passing hole 10a is a circular through hole that allows the electron beam EB emitted from the electron gun EG to pass therethrough. The passing hole 10a extends along an emission direction of the electron beam EB. The passing hole 10a communicates with the inside of a first tubular member 21 (to be described later) of the rod portion 20. A vacuum pump 50 is connected to the main body portion 10 via an exhaust passage 10b. The inside of the main body portion 10 can be easily evacuated by the vacuum pump 50.

A proximal end side of the rod portion 20 is detachably connected to the main body portion 10. The rod portion 20 extends such that a distal end side thereof protrudes from the main body portion 10. The rod portion 20 extends to be away from the main body portion 10 along the emission direction of the electron beam EB of the electron gun EG. The rod portion 20 communicates with the inside of the main body portion 10. The rod portion 20 forms a space through which the electron beam EB emitted from the electron gun EG passes. Details of the configuration of the rod portion 20 will be described later.

Figure 2:
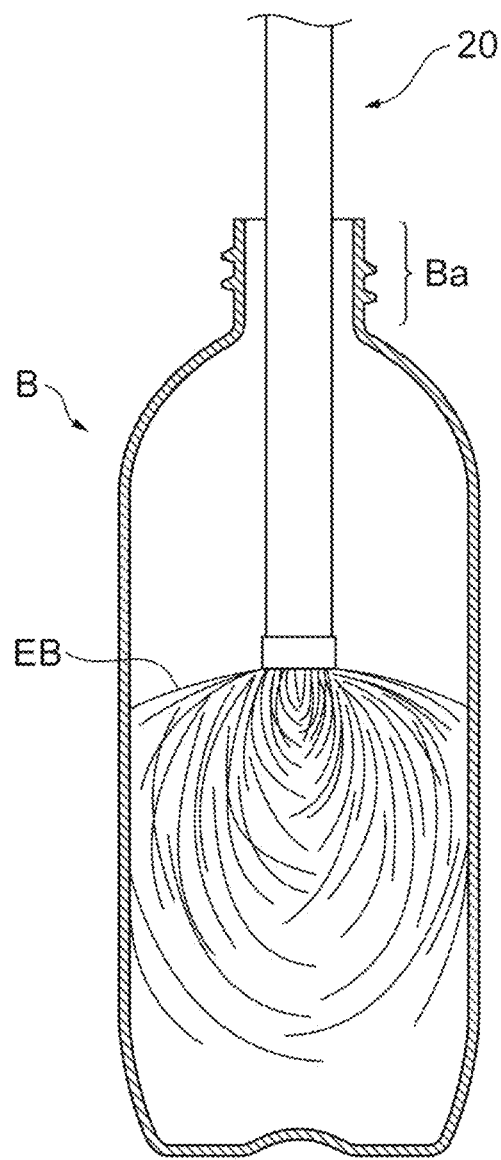
FIG. 2 is a view illustrating an example of use of the electron beam irradiation device of FIG. 1.

FIG. 2 is a view illustrating an example of use of the electron beam irradiation device of FIG. 1. The rod portion 20 is configured to be insertable into a bottle B via a mouth portion Ba of the bottle B which is a container. The bottle B to be applied is not particularly limited, and various bottles B can be applied. A size, a material, a shape, appearance and usage or the like of the bottle B are not limited, and various bottles can be applied. As the bottle B of the present embodiment, a beverage bottle having a capacity of two liters is applied. In the illustrated example, the bottle B is the container including the mouth portion Ba which is an opening portion. An inner diameter of the mouth portion Ba is smaller than an outer shape of the main body portion 10 and larger than an outer diameter of the rod portion 20. That is, the rod portion 20 has the outer diameter that can be inserted into the mouth portion Ba of the bottle B along an axial direction of the bottle B. A length of the rod portion 20 is set to such a length that a distal end of the rod portion 20 can reach the vicinity of a bottom surface of the bottle B such that the bottom surface of the bottle B is irradiated with the electron beam EB.

As illustrated in FIG. 1, the electron beam emission window 11 is provided on the distal end side of the rod portion 20. The electron beam emission window 11 transmits the electron beam EB that has passed through the rod portion 20, and emits the electron beam EB toward the outside. The electron beam emission window 11 is a circular thin-film member. The electron beam emission window 11 is made of a material (for example, beryllium, titanium, aluminum, or the like) that transmits the electron beam EB. A thickness of the electron beam emission window 11 is, for example, 15 μm or smaller.

The control unit 12 is constituted by one or more computer devices having, for example, a processor and a storage device (a memory and the like). The control unit 12 operates in accordance with a program stored in the storage device and controls each unit of the electron beam irradiation device 1a.

The adjusting electromagnetic coil 13 is an adjustment unit that adjusts an orbit (emission axis) of the electron beam EB. The adjusting electromagnetic coil 13 functions as an electromagnetic lens. The adjusting electromagnetic coil 13 deflects an advancing direction of the electron beam EB passing through the passing hole 10a of the main body portion 10 such that the electron beam EB emitted from the electron gun EG reaches the electron beam emission window 11. For example, the adjusting electromagnetic coil 13 performs fine adjustments such that the emission axis of the electron beam EB roughly coincides with a central axis of the rod portion 20. The adjusting electromagnetic coil 13 is connected to the control unit 12, and a current flowing thereto is controlled by the control unit 12. As a result, the fine adjustment of the orbit of the electron beam EB is realized. The adjusting electromagnetic coil 13 is arranged outside the vacuum space Z. The adjusting electromagnetic coil 13 is annularly arranged so as to surround the passing hole 10a of the main body portion 10.

The converging electromagnetic coil 14 is a converging unit that controls converging of the electron beam EB. The converging electromagnetic coil 14 functions as an electromagnetic lens. For example, the converging electromagnetic coil 14 suppresses spreading of the electron beam EB which advances so as to spread along the emission axis and performs converging control such that an irradiation range of the electron beam EB on the electron beam emission window 11 is constant. The converging electromagnetic coil 14 is connected to the control unit 12, and a current flowing thereto is controlled by the control unit 12. As a result, the fine adjustment of the converging control of the electron beam EB is realized.

The converging electromagnetic coil 14 is arranged outside the vacuum space Z at a position closer to the electron beam emission side than the adjusting electromagnetic coil 13. That is, the adjusting electromagnetic coil 13 and the converging electromagnetic coil 14 are arranged in this order along the emission direction of the electron beam EB. The electron beam emission side is a side on which the electron beam EB is emitted (the lower side in FIG. 1). The electron beam emission side is an advancing side of the electron beam EB. In other words, the electron beam emission side is the front side in the advancing direction of the electron beam EB. The adjusting electromagnetic coil 13 is annularly arranged so as to surround the passing hole 10a of the main body portion 10 on the electron beam emission side of the converging electromagnetic coil 14.

Next, the configuration of the rod portion 20 will be described in detail with reference to FIGS. 3 to 6.

Figure 3:
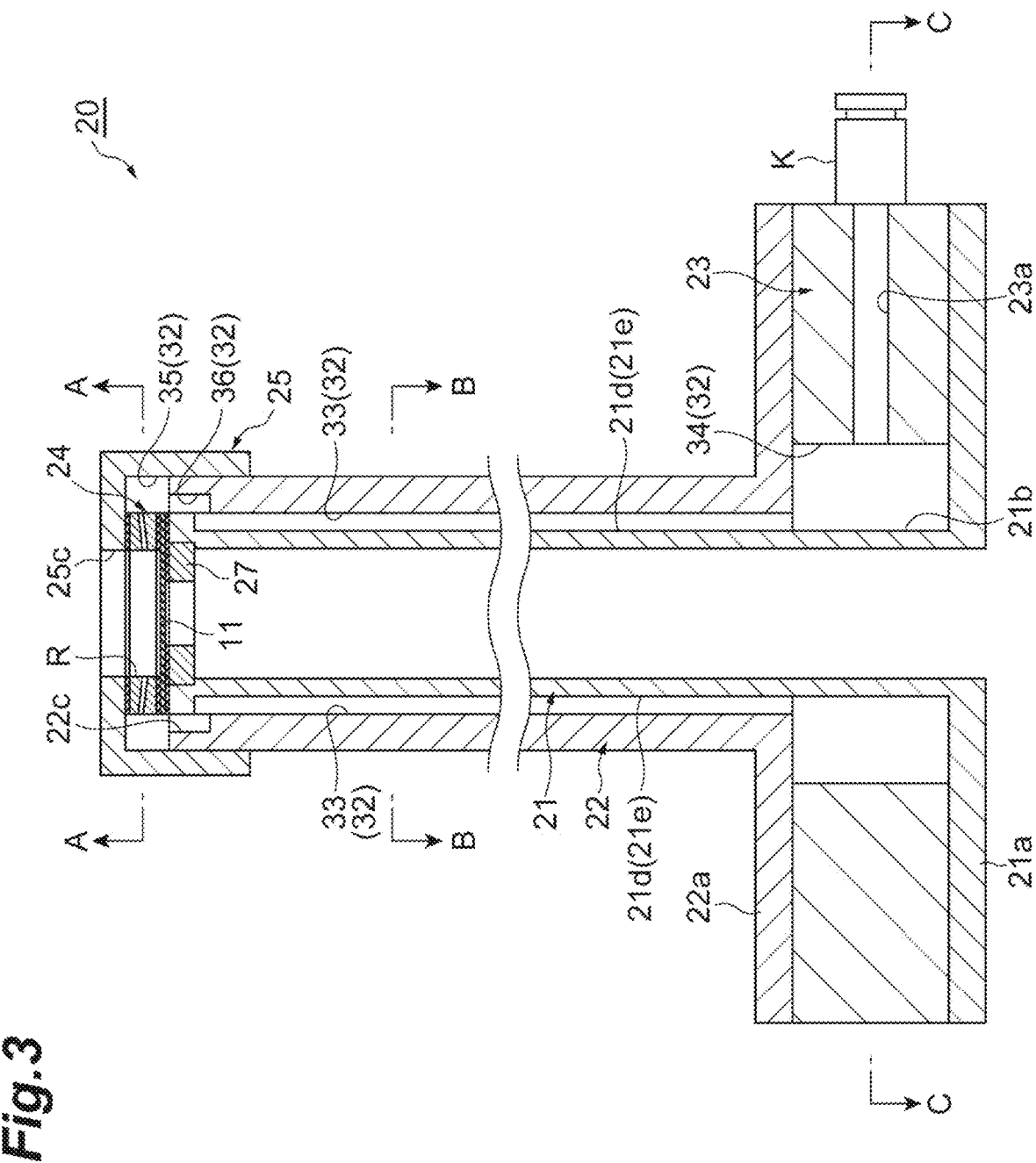
FIG. 3 is a cross-sectional view illustrating a rod portion of FIG. 1.
Figure 4:
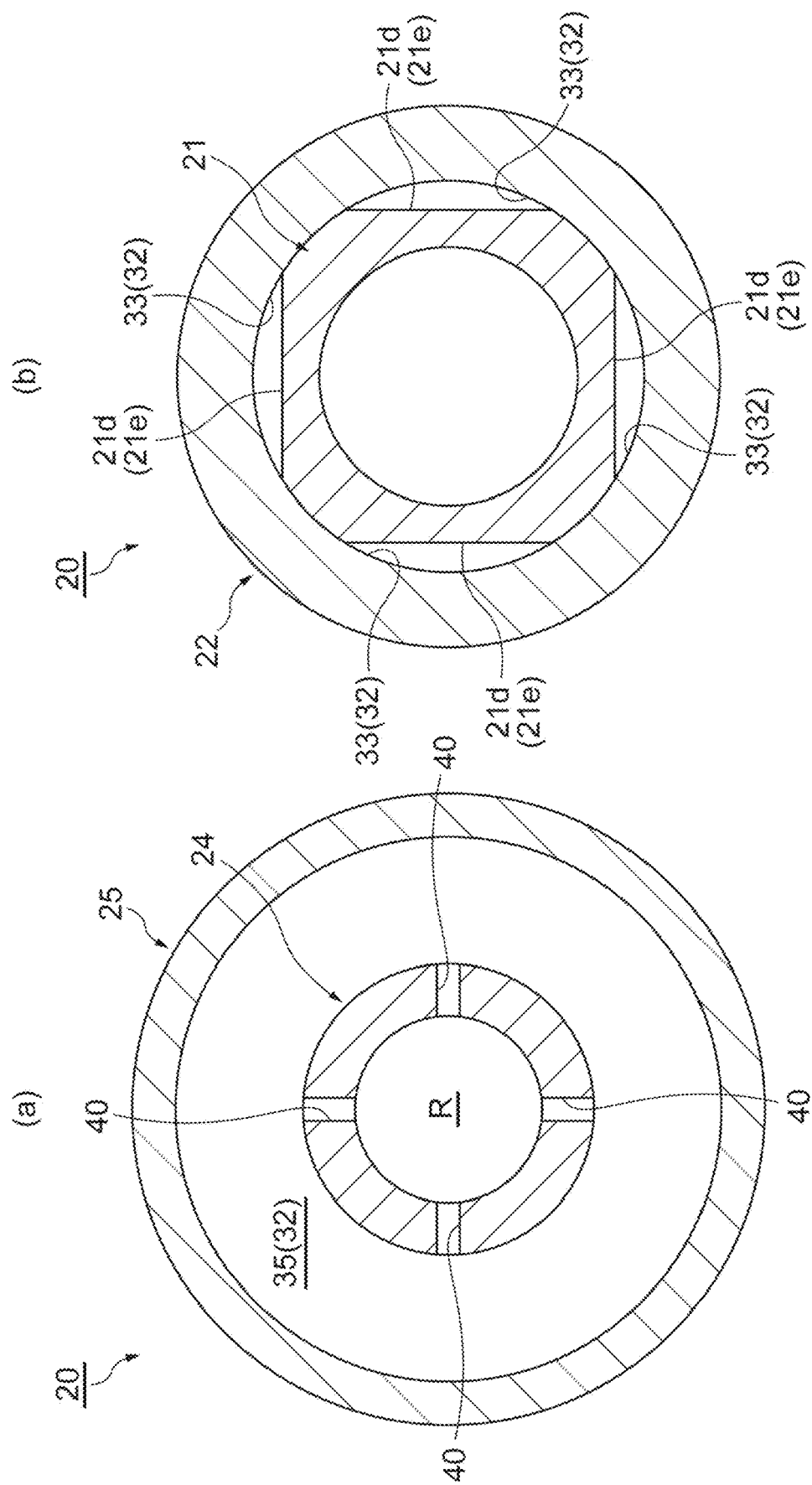
FIG. 4(*a*) is a cross-sectional view taken along line A-A of FIG. 3.
Figure 5:
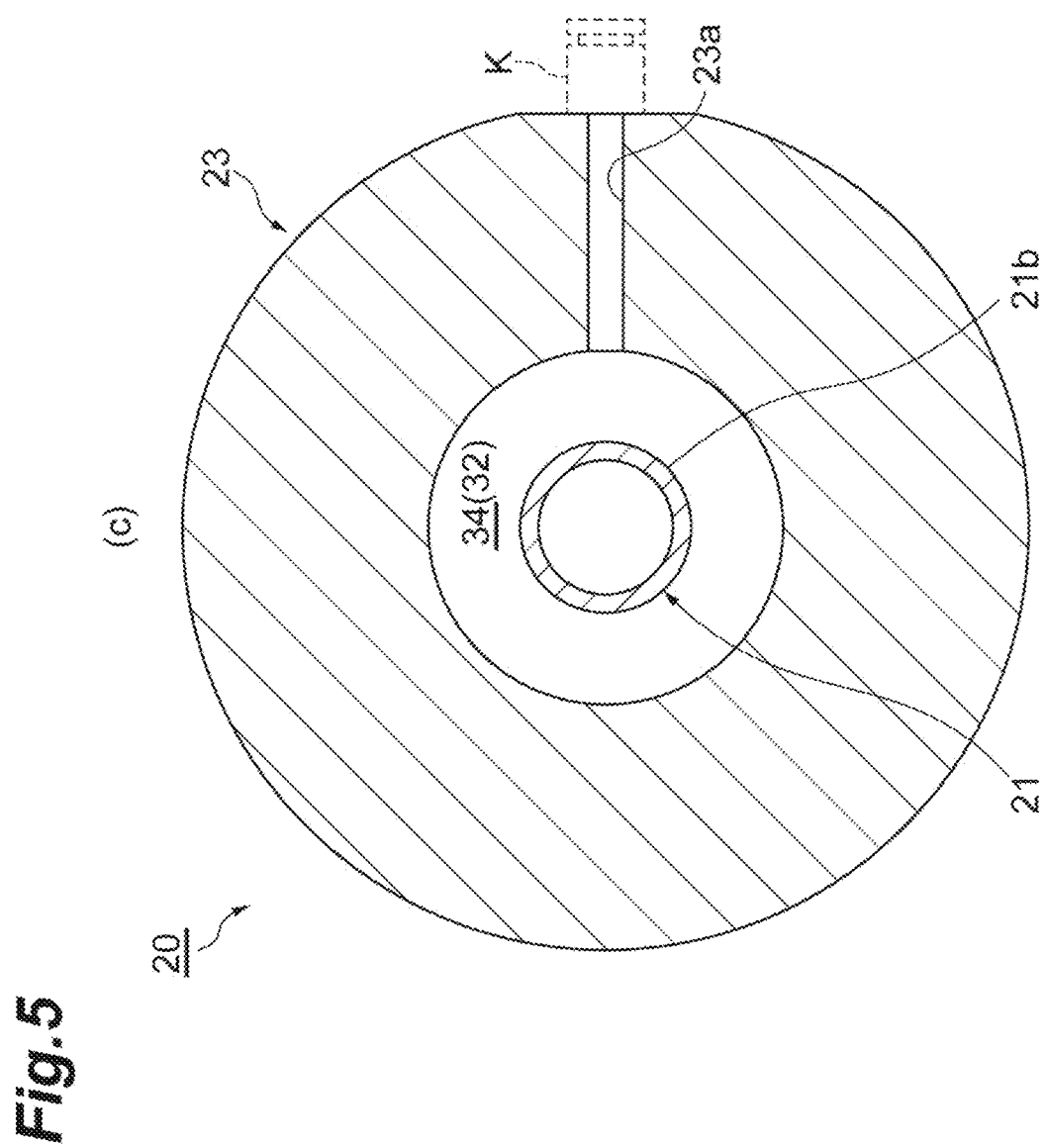
FIG. 5 is a cross-sectional view taken along line C-C of FIG. 3.
Figure 6:
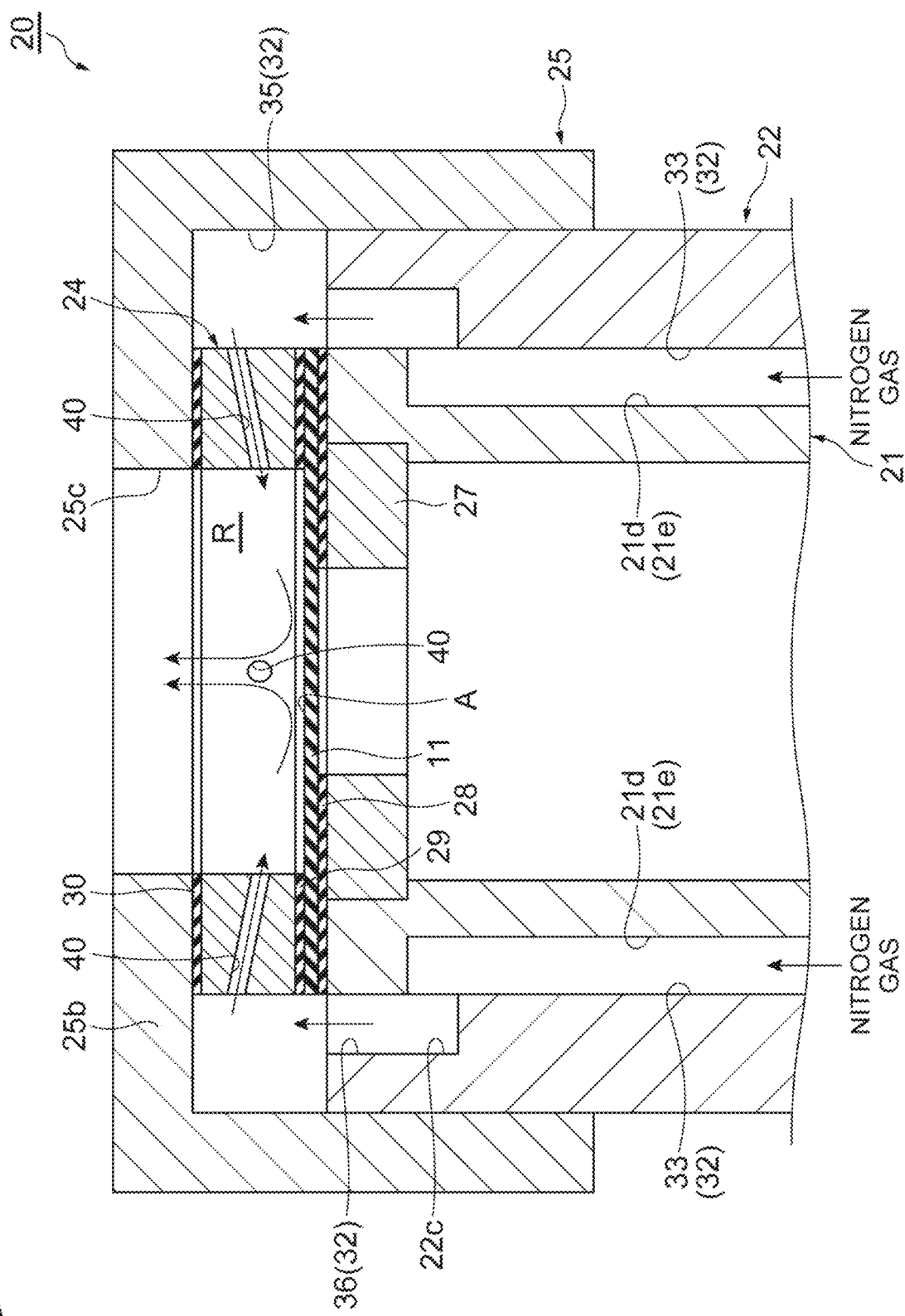
FIG. 6 is an enlarged cross-sectional view illustrating a distal end side of the rod portion in FIG. 1.

FIG. 3 is a cross-sectional view illustrating the rod portion 20 of FIG. 1. FIG. 4(a) is a cross-sectional view taken along line A-A in FIG. 3. FIG. 4(b) is a cross-sectional view taken along line B-B of FIG. 3. FIG. 5 is a cross-sectional view taken along line C-C of FIG. 3. FIG. 6 is an enlarged cross-sectional view illustrating the distal end side of the rod portion 20 of FIG. 1. Incidentally, each of the cross-sectional views illustrated in FIGS. 4(a), 4(b), and 5 is appropriately expanded for convenience of description. Scales of FIGS. 4(a), 4(b), and 5 are not the same. Hereinafter, the distal end side of the rod portion 20 will be simply referred to as the "distal end side", and the proximal end side of the rod portion 20 will be simply referred to as the "proximal end side".

As illustrated in FIG. 3, the rod portion 20 includes the first tubular member 21, a second tubular member 22, a fixing member 23, a wall member 24, and a pressing member 25. The first tubular member 21 has a tubular shape with the extending direction of the rod portion 20 (that is, the emission direction of the electron beam EB) as an axial direction. Here, the first tubular member 21 has a cylindrical shape. The electron beam EB emitted from the electron gun EG passes through the inside of the first tubular member 21. The first tubular member 21 is formed of a metallic material (a nonmagnetic material, for example, stainless steel, aluminum, oxygen-free copper or the like) capable of reliably holding a vacuum. On the other hand, the second tubular member 22 is formed of a magnetic material capable of shielding an external magnetic field, such as geomagnetism, which is applied to the electron beam EB inside the first tubular member 21. As the magnetic material, permalloy, PC permalloy, or the like can be used.

The first tubular member 21 is arranged so as to communicate with the passing hole 10a of the main body portion 10. A flange 21a protruding outward in the radial direction is provided at an end portion on the proximal end side of the first tubular member 21. The first tubular member 21 is detachably fixed to the main body portion 10 by fastening the flange 21a to the main body portion 10 with a screw or the like.

An annular concave portion 21b, which is a concave portion along the entire circumference in the circumferential direction, is formed at the end portion on the proximal end side on an outer circumferential surface of the first tubular member 21. As illustrated in FIGS. 3 and 4(b), a plurality of separating portions 21d is formed in a region other than the end portion on the distal end side and the end portion on the proximal end side on the outer circumferential surface of the first tubular member 21. In particular, the plurality of separating portions 21d extending along the axial direction of the first tubular member 21 is juxtaposed in the circumferential direction in the region from the distal end side of the annular concave portion 21b to a distal end edge of the outer circumferential surface on the outer circumferential surface of the first tubular member 21.

The separating portion 21d is provided so as to cut out a part of the circular outer circumferential surface side of the first tubular member 21 to be chamfered into an arcuate shape in a cross section perpendicular to the axial direction of the first tubular member 21. The separating portion 21d includes a planar surface 21e which extends along the axial direction of the first tubular member 21 and has a rectangular planar shape. The separating portions 21d are provided at four positions (four equal positions) equally spaced in the circumferential direction on the outer circumferential surface of the first tubular member 21. With the above separating portion 21d, two pairs of the planar surfaces 21e having the planar shape and facing each other are formed in the region other than the end portion on the distal end side and the end portion on the proximal end side on the outer circumferential surface of the first tubular member 21. An outer wall surface of the first tubular member 21 is formed of an outer circumferential surface which is a side surface of a cylindrical shape and the four planar surfaces 21e.

As illustrated in FIGS. 3 and 6, a cylindrical support member 27 that supports the electron beam emission window 11 is provided at the end portion on the distal end side of an inner circumferential surface of the first tubular member 21. The support member 27 is arranged coaxially with the first tubular member 21. An end face on the distal end side of the support member 27 is positioned on the same plane as an end face on the distal end side of the first tubular member 21. The support member 27 supports the electron beam emission window 11 from the proximal end side against external atmosphere.

The electron beam emission window 11 is provided at the end portion on the distal end side of the first tubular member 21. Specifically, the electron beam emission window 11 is arranged on the end face on the distal end side of the first tubular member 21 and on the end face on the distal end side of the support member 27 with an annular film-like sheet material 28 interposed therebetween. In other words, the electron beam emission window 11 is superimposed on the distal end side of the first tubular member 21 and the distal end side of the support member 27 with the sheet material 28 interposed therebetween so as to close an opening at the distal end of the first tubular member 21. In the illustrated example, a distal end outer diameter of the first tubular member 21 coincides with an outer diameter of the electron beam emission window 11. As the sheet material 28, a graphite sheet excellent in heat dissipation property and airtight retention property can be used. A central region corresponding to an inner hole of the support member 27 in the electron beam emission window 11 forms an electron beam emission region A to which the electron beam EB is emitted.

As illustrated in FIG. 3, the second tubular member 22 has a tubular shape with the extending direction of the rod portion 20 as an axial direction. Here, the second tubular member 22 has a cylindrical shape. The second tubular member 22 surrounds the first tubular member 21. The second tubular member 22 is arranged coaxially with the first tubular member 21 on the outer side of the first tubular member 21. As a result, the first tubular member 21 and the second tubular member 22 form a double tube structure.

As illustrated in FIGS. 3 and 4(b), an inner diameter of the second tubular member 22 corresponds to an outer diameter of the first tubular member 21. An inner circumferential surface which is an inner wall surface of the second tubular member 22 is separated from the planar surface 21e of the first tubular member 21 and a gap is formed therebetween. On the other hand, the inner circumferential surface of the second tubular member 22 is in contact with the outer circumferential surface of the first tubular member 21 (an arcuate surface portion of an outer wall surface excluding the planar surface 21e). That is, the inner circumferential surface of the second tubular member 22 is in contact with the outer circumferential surface of the first tubular member 21 at at least two points, in the cross section perpendicular to the extending direction of the rod portion 20. In the present embodiment, contact points between the inner circumferential surface of the second tubular member 22 and the outer circumferential surface of the first tubular member 21 includes two sets of two points facing each other, that is, four points adjacent to the separating portion 21d. The contact point may be a point-contact point, a line-contact point, or a surface-contact point.

An end face on the distal end side of the second tubular member 22 is positioned on the same plane as the end face on the distal end side of the first tubular member 21. A flange 22a protruding outward in the radial direction is provided at an end portion on the proximal end side of the second tubular member 22. The flange 22a has an outer diameter equal to the outer diameter of the flange 21a of the first tubular member 21. The flange 22a is positioned at a position corresponding to the end portion on the proximal end side of the separating portion 21d. A female screw (not illustrated) to be screwed with the pressing member 25 is formed at the end portion on the distal end side of the outer circumferential surface of the second tubular member 22. An opening portion 22c which has a circular cross section and is open towards the distal end side is formed at the end portion on the distal end side of the inner circumferential surface of the second tubular member 22. An inner circumferential surface of the opening portion 22c faces the end portion on the distal end side of the outer circumferential surface of the first tubular member 21 with a gap therebetween.

As illustrated in FIGS. 3 and 5, the fixing member 23 has a cylindrical shape coaxial with the first tubular member 21 and the second tubular member 22. The fixing member 23 is arranged between the flange 21a of the first tubular member 21 and the flange 22a of the second tubular member 22. The fixing member 23 is fixed to the first tubular member 21 and the second tubular member 22 by a screw or the like. The fixing member 23 has an outer diameter equal to the outer diameter of the flange 21a and the flange 22a. The first tubular member 21 is inserted through the inside of the fixing member 23. The fixing member 23 surrounds the periphery of the annular concave portion 21b of the first tubular member 21 with a gap therebetween. The fixing member 23 may be formed integrally with any one of the first tubular member 21 and the second tubular member 22.

As illustrated in FIGS. 4(a) and 6, the wall member 24 has a cylindrical shape coaxial with the first tubular member 21 and the second tubular member 22. The wall member 24 is arranged on an outer edge portion on the electron beam emission side of the electron beam emission window 11 with an annular film-like sheet material 29 interposed therebetween. As the sheet material 29, a graphite sheet excellent in heat dissipation property and airtight retention property can be used. The wall member 24 defines an electron beam emission space R which is a columnar space facing the electron beam emission side of the electron beam emission window 11. The electron beam emission space R is an external space outside the rod portion 20. The wall member 24 is provided so as to perform partition between the electron beam emission space R and a cooling gas flow space 32 to be described later.

The pressing member 25 has a bottomed cylindrical shape which is open toward the proximal end side. A male screw (not illustrated) is formed on an inner circumferential surface of the pressing member 25. The pressing member 25 is detachably fixed to the distal end side of the second tubular member 22 by screwing the male screw with the female screw on the outer circumferential surface of the second tubular member 22. The pressing member 25 surrounds the periphery of the second tubular member 22. The pressing member 25 surrounds the periphery of the wall member 24 with a gap therebetween.

A bottom portion 25b of the pressing member 25 abuts against an end face on the distal end side of the wall member 24 via an annular film-like sheet material 30. As a result, the pressing member 25 presses the wall member 24 toward the electron beam emission window 11 to fix the electron beam emission window 11 to the first tubular member 21 such that the inside of the first tubular member 21 is vacuum-sealed. As the sheet material 30, a graphite sheet excellent in heat dissipation property and airtight retention property can be used. A through hole 25c having a circular cross section is formed in the axial position of the pressing member 25. The through hole 25c has the same inner diameter as the inner diameter of the wall member 24. The through hole 25c communicates with the electron beam emission space R.

As illustrated in FIGS. 3 and 6, the rod portion 20 of the present embodiment has the cooling gas flow space 32. The cooling gas flow space 32 is for a cooling gas introduced from the proximal end side to flow to the distal end side. Examples of the cooling gas include a nitrogen gas, an argon gas, an ozone gas, or other inert gases although not particularly limited. The cooling gas herein is the nitrogen gas. The cooling gas flow space 32 includes a plurality of cooling gas flow paths 33, a proximal end space 34, a distal end space 35, and a relay flow path 36.

The cooling gas flow path 33 is formed by a gap between the separating portion 21d (the planar surface 21e) of the first tubular member 21 and the inner circumferential surface of the second tubular member 22. That is, the separating portion 21d separates the outer circumferential surface of the first tubular member 21 from the inner circumferential surface of the second tubular member 22 so as to form the cooling gas flow path 33, in the cross section perpendicular to the extending direction of the rod portion 20. The cooling gas flow path 33 has a space of an arc shape having an arc on the outer side in the radial direction in the cross section perpendicular to the extending direction of the rod portion 20. The cooling gas flow path 33 straightly extends along the extending direction of the rod portion 20. The cooling gas flow path 33 allows the nitrogen gas to flow from the proximal end side to the distal end side. A plurality of the cooling gas flow paths 33 corresponding to the number of the separating portions 21d is formed. The cooling gas flow paths 33 are provided at four positions equally spaced in the circumferential direction of the rod portion 20. That is, two pairs of the cooling gas flow paths 33 facing each other are formed.

The proximal end space 34 is formed on the proximal end side of the rod portion 20. The proximal end space 34 is a cylindrical space formed around the first tubular member 21. The proximal end space 34 is formed by a gap between the inner circumferential surface of the annular concave portion 21b of the first tubular member 21 and the inner circumferential surface of the fixing member 23. Specifically, the proximal end space 34 is defined (formed to be partitioned) by the annular concave portion 21b of the first tubular member 21, the flange 21a of the first tubular member 21, the flange 22a of the second tubular member 22, and the inner circumferential surface of the fixing member 23. The proximal end space 34 communicates with the plurality of cooling gas flow paths 33.

A nitrogen gas is introduced into the proximal end space 34 from the outside of the rod portion 20. Specifically, the configuration in which the nitrogen gas is introduced into the proximal end space 34 is configured as follows. That is, a gas introduction hole 23a, which penetrates the inner circumferential surface and the outer circumferential surface of the fixing member 23 and extends in the radial direction, is formed in the fixing member 23 so as to make the proximal end space 34 communicate with the outside. A nitrogen gas generator 37 (see FIG. 1) is connected to the gas introduction hole 23a via a gas introduction portion K. As a result, the nitrogen gas generated by the nitrogen gas generator 37 is introduced into the proximal end space 34 from the gas introduction portion K via the gas introduction hole 23a.

The distal end space 35 is formed on the distal end side of the rod portion 20. The distal end space 35 is a cylindrical space formed around the wall member 24. The distal end space 35 is formed by a gap between the outer circumferential surface of the wall member 24 and an inner circumferential surface of the pressing member 25. Specifically, the distal end space 35 is defined by the end faces of the distal end side of the wall member 24, the pressing member 25, and the second tubular member 22. The distal end space 35 communicates with a plurality of cooling gas ejection holes 40 (to be described later) formed in the wall member 24. The distal end space 35 communicates with the plurality of cooling gas flow paths 33 via the relay flow path 36. That is, the distal end space 35 causes the plurality of cooling gas ejection holes 40 to communicate with the plurality of cooling gas flow paths 33.

The relay flow path 36 is formed by a gap between the end portion on the distal end side of the outer circumferential surface of the first tubular member 21 and the inner circumferential surface of the opening portion 22c of the second tubular member 22. The relay flow path 36 is a cylindrical space. The relay flow path 36 is provided between the cooling gas flow path 33 and the distal end space 35. The relay flow path 36 communicates with the cooling gas flow path 33 and communicates with the distal end space 35. The relay flow path 36 causes the nitrogen gas flowing through the cooling gas flow path 33 to flow into the distal end space 35.

As illustrated in FIGS. 4(a) and 6, the wall member 24 is provided with the plurality of cooling gas ejection holes 40 that ejects the nitrogen gas from the cooling gas flow space 32 to the electron beam emission space R in the rod portion 20 of the present embodiment. The cooling gas ejection hole 40 is a through hole having a circular cross section. The cooling gas ejection hole 40 penetrates from the outer circumferential surface to the inner circumferential surface of the wall member 24. The cooling gas ejection hole 40 extends along the radial direction of the wall member 24. An inner diameter of the cooling gas ejection hole 40 is constant from one end to the other end. The cooling gas ejection hole 40 communicates with the distal end space 35 of the cooling gas flow space 32 and communicates with the electron beam emission space R. The cooling gas ejection hole 40 is provided at four positions equally spaced in the circumferential direction of the wall member 24. That is, the wall member 24 has two sets of the pair of cooling gas ejection holes 40 facing each other with the central axis of the wall member 24 interposed therebetween.

The cooling gas ejection hole 40 has a flow path sectional area smaller than a flow path sectional area of one cooling gas flow path 33. In other words, the cooling gas ejection holes 40 is smaller than each of the plurality of cooling gas flow paths 33 regarding a sectional area of a cross section perpendicular to a flowing direction of the nitrogen gas. Incidentally, it is sufficient if a flow path sectional area at any position from one end to the other end of the cooling gas ejection hole 40 is smaller than the flow path sectional area of the cooling gas flow path 33. The expression, "smaller than the flow path sectional area of the cooling gas flow path 33" includes a case of being smaller than a flow path sectional area at any position from one end to the other end of the cooling gas flow path 33. That is, the expression includes a case where a minimum flow path sectional area of the cooling gas ejection hole 40 is smaller than a maximum flow path sectional area of the single cooling gas flow path 33.

The cooling gas ejection hole 40 is formed in a central portion of the wall member 24 in the extending direction of the rod portion 20 (a height direction of the wall member 24). The cooling gas ejection hole 40 is inclined to the proximal end side toward the inner side in the radial direction. An opening on the inner side in an inclination direction of the cooling gas ejection hole 40 faces the electron beam emission region A of the electron beam emission window 11. Here, the electron beam emission region A of the electron beam emission window 11 is positioned on an extension line obtained by extending the central axis of the cooling gas ejection hole 40 to the inner side in the radial direction. As a result, the cooling gas ejection hole 40 ejects the nitrogen gas toward the electron beam emission region A of the electron beam emission window 11 to cool the electron beam emission window 11 (in particular, the electron beam emission region A).

Next, an operation example of the electron beam irradiation device 1 having the above configuration will be described.

After the inside of the main body portion 10 is evacuated by the vacuum pump 50 to form the vacuum space Z, the filament 7 is preliminarily heated by energizing the filament 7 to prepare for electron emission. Subsequently, a power-supply voltage of minus several kV to minus several 100 kV is applied from the power supply device. This power-supply voltage is supplied to the filament 7 via the internal wirings 9a and 9b. Then, the filament 7 is heated to such a temperature that a desired tube current value can be obtained. Thereafter, electrons are extracted from the filament 7 by the grid portion 8 and emitted.

The electrons emitted from the filament 7 are suppressed from being diffused by the grid portion 8 and become the electron beams EB having energy corresponding to the applied voltage. The electron beam EB advances straight to spread and advances toward the electron beam emission window 11 inside the rod portion 20. After the orbit of the electron beam EB is finely adjusted by the adjusting electromagnetic coil 13, the converging control of the electron beam EB is performed by the converging electromagnetic coil 14 such that no convergence point is formed inside the rod portion 20. Thereafter, the electron beam EB reaches the electron beam emission window 11, passes through the electron beam emission window 11, and is emitted to the outside of the electron beam irradiation device 1. After the electron beam EB is turned into the emission state, the distal end side of the rod portion 20 is inserted into the bottle B via the mouth portion Ba of the bottle B. As a result, an inner surface of the bottle B is efficiently irradiated with the electron beam EB so that the inner surface of the bottle B is sterilized.

Simultaneously with such irradiation of the electron beam EB, the electron beam emission window 11 on the distal end side of the extending rod portion 20 is cooled as follows. That is, a nitrogen gas is pressure-fed from the nitrogen gas generator 37, and the nitrogen gas is introduced into the proximal end space 34 from the gas introduction portion K via the gas introduction hole 23a. The nitrogen gas inside the proximal end space 34 flows into the plurality of cooling gas flow paths 33 and flows from the proximal end side to the distal end side in each of the cooling gas flow paths 33. The nitrogen gas that has passed through each of the cooling gas flow paths 33 flows into the distal end space 35 via the relay flow path 36. The nitrogen gas in the distal end space 35 flows into the plurality of cooling gas ejection holes 40 and is blown from each of the cooling gas ejection holes 40 to the electron beam emission space R. As a result, the nitrogen gas is brought into contact with the electron beam emission window 11 and directly cools the electron beam emission window 11. Thereafter, the nitrogen gas flows while changing its direction to the distal end side, and diffuses into the external atmosphere.

Incidentally, a heat flow rate (the amount of carried heat) in air cooling increases as the velocity and the pressure (dynamic pressure) of the cooling gas increase. Therefore, it is found that the cooling efficiency increases as the pressure of the cooling gas in contact with the electron beam emission window 11 increases. When a flow path sectional area is made small, the cooling efficiency is improved since the velocity of the cooling gas increases if the flow rate is the same. However, when the flow path sectional area is simply reduced, a pressure loss becomes large so that the cooling gas hardly flows.

Therefore, in the electron beam irradiation device 1, the cooling gas ejection hole 40 has the flow path sectional area smaller than the flow path sectional area of the cooling gas flow path 33. As a result, the nitrogen gas is reliably caused to flow in the cooling gas flow path 33, and thereafter, the nitrogen gas is ejected by the cooling gas ejection hole 40 having a small flow path sectional area so that it is possible to increase the pressure of the ejected nitrogen gas. That is, it is possible to directly supply the nitrogen gas having a high pressure to the electron beam emission window 11. Therefore, it is possible to efficiently cool the electron beam emission window 11 provided on the distal end side of the extending rod portion 20. It is possible to suppress damage caused by the heat generation of the electron beam emission window 11, and the durability of the electron beam emission window 11 can be significantly improved.

Incidentally, a water-cooling cooling structure, which cools the electron beam emission window 11 by flowing cooling water at a flow rate at which sufficient cooling efficiency can be obtained is also conceivable to efficiently cool the electron beam emission window 11. However, there is a limitation on the thickness of the rod portion 20 in order to insert the rod portion 20 inside the bottle B, and thus, there is a possibility that it is extremely difficult to provide the water-cooling cooling structure on the rod portion 20. In regard to this, the air cooling, which directly cools the electron beam emission window 11 using the nitrogen gas as a cooling medium, is performed in the electron beam irradiation device 1. In the case of the air cooling, it is easy to bring the cooling medium directly into contact with the electron beam emission window 11 as compared with the case of the water cooling. Therefore, the electron beam emission window 11 can be efficiently cooled even if there is a limitation on the thickness of the rod portion 20, and thus, it is possible to increase the cooling efficiency of the electron beam emission window 11 while maintaining a small diameter of the rod portion 20.

Since it is possible to directly cool the electron beam emission window 11 with the high-pressure nitrogen gas, it is possible to reduce the necessity of widening a flow path of the nitrogen gas to increase a flow rate in order to enhance the cooling efficiency of the electron beam emission window 11. When there is a limitation on the thickness of the rod portion 20, the effect that it is possible to reduce the necessity of widening the flow path of the nitrogen gas is particularly advantageous.

In the electron beam irradiation device 1, the cooling gas ejection hole 40 ejects the nitrogen gas toward the electron beam emission region A of the electron beam emission window 11. As a result, the nitrogen gas is directly blown to the portion of the electron beam emission window 11 where the temperature is the highest, whereby it is possible to more efficiently cool the electron beam emission window 11.

In the electron beam irradiation device 1, the plurality of cooling gas ejection holes 40 is provided in the wall member 24. The cooling gas flow space 32 includes the distal end space 35. The distal end space 35 functions as a gas reservoir and the nitrogen gas from the cooling gas flow path 33 can be stored in the distal end space 35. As a result, the nitrogen gas can be supplied to the plurality of cooling gas ejection holes 40 from the common distal end space 35. The respective states of the nitrogen gases ejected from the plurality of cooling gas ejection holes 40 can be made uniform. As a result, it is possible to perform the cooling with less deviation with respect to the electron beam emission window 11.

In the electron beam irradiation device 1, the cooling gas flow space 32 includes the plurality of cooling gas flow paths 33 and the proximal end space 34. The proximal end space 34 functions as a gas reservoir and the nitrogen gas introduced from the outside can be stored in the proximal end space 34. As a result, the cooling gas can be supplied to the plurality of cooling gas flow paths 33 from the common proximal end space 34. The respective states of the nitrogen gases flowing through the plurality of cooling gas flow paths 33 can be made uniform. As a result, it is possible to perform the cooling with less deviation with respect to the electron beam emission window 11.

In the electron beam irradiation device 1, the separating portion 21d, which separates the outer circumferential surface from the inner circumferential surface of the second tubular member 22 so as to form the cooling gas flow path 33, is formed on the outer circumferential surface of the first tubular member 21, in the cross section perpendicular to the extending direction of the rod portion 20. The outer circumferential surface of the first tubular member 21 and the inner circumferential surface of the second tubular member 22 are in contact with each other at at least two points in the cross section perpendicular to the extending direction of the rod portion 20. As a result, it is possible to prevent the cooling gas flow path 33 from being narrowed or widened when the force to change the distance between the first tubular member 21 and the second tubular member 22 is applied due to an external factor and the like during the operation, for example or even when a variation or deviation occurs in structure due to assembly accuracy. The cooling gas flow path 33 can be maintained with high accuracy. It is possible to make the nitrogen gas to stably flow through the cooling gas flow path 33. It is possible to stably cool the electron beam emission window 11.

In addition, it is possible to easily perform positioning of the first tubular member 21 with respect to the second tubular member 22 and positioning of the second tubular member 22 with respect to the first tubular member 21 since the outer circumferential surface of the first tubular member 21 and the inner circumferential surface of the second tubular member 22 are in contact with each other at at least two points in this manner.

In the electron beam irradiation device 1, the separating portion 21d is formed on the outer circumferential surface of the first tubular member 21. As a result, it is possible to easily form the separating portion 21d as compared with the case where the separating portion 21d is formed on the inner circumferential surface of the second tubular member 22.

The electron beam irradiation device 1 includes the adjusting electromagnetic coil 13 and the converging electromagnetic coil 14. As the orbit and the converging of the electron beam EB are appropriately adjusted by the adjusting electromagnetic coil 13 and the converging electromagnetic coil 14, it is possible to prevent the electron beam EB from being incident on the inner circumferential surface of the first tubular member 21, and to efficiently guide the electron beam EB to the electron beam emission window 11. It is possible to suppress heat generation of the rod portion 20. It is possible to prevent the nitrogen gas flowing through the cooling gas flow path 33 from being heated by the heat generation. As a result, it is possible to suppress a temperature rise of the nitrogen gas reaching the electron beam emission window 11 due to the heating. It is possible to more efficiently cool the electron beam emission window 11.

In the electron beam irradiation device 1, the second tubular member 22 is made of a magnetic material. As a result, the second tubular member 22 functions as a magnetic shield, and it is possible to suppress the influence of the external magnetic field on the electron beam EB passing through the inside of the first tubular member 21. Specifically, it is possible to shield the external magnetism, such as geomagnetism, which is applied to the electron beam EB in the first tubular member 21, and to suppress the deviation of the orbit of the electron beam EB. Incidentally, the first tubular member 21 may be formed using a magnetic material instead of the second tubular member 22, or both the first tubular member 21 and the second tubular member 22 may be formed using a magnetic material. In addition, the rod portion 20 may be covered additionally with a magnetic material.

In the electron beam irradiation device 1, the electron beam emission window 11 is arranged on the end face on the distal end side of the first tubular member 21. The wall member 24 is arranged on the electron beam emission side of the electron beam emission window 11. The pressing member 25 detachably fixed to the second tubular member 22 presses the wall member 24 toward the electron beam emission window 11. As a result, it is possible to press and fix the electron beam emission window 11 using the wall member 24 provided with the cooling gas ejection holes 40. In addition, it is possible to easily replace the electron beam emission window 11 by detaching the pressing member 25.

In the electron beam irradiation device 1, the electron beam emission window 11 is provided on the end face of the first tubular member 21 with the sheet material 28 interposed therebetween. The wall member 24 is provided on the electron beam emission window 11 with the sheet material 29 interposed therebetween. The inside of the first tubular member 21 can be hermetically sealed by the sheet material 28. The distal end space 35 can be hermetically sealed by the sheet material 29.

In the electron beam irradiation device 1, the pressing member 25 is provided on the wall member 24 with the sheet material 30 interposed therebetween. The distal end space 35 can be hermetically sealed by the sheet material 30. In addition, when the pressing member 25 is rotated at the time of attachment or detachment, the sheet material 30 does not rotate together with the pressing member 25 in order to slide with respect to the pressing member 25, and thus, it is possible to suppress a rotational force from being applied to the wall member 24 when the pressing member 25 has been rotated.

In the electron beam irradiation device 1, the nitrogen gas blown from the cooling gas ejection holes 40 flows and diffuses to the external atmosphere. Therefore, a mechanism for circulating the nitrogen gas in the rod portion 20 can be made unnecessary. As a result, a mechanism for dissipating the nitrogen gas can be made unnecessary.

In the electron beam irradiation device 1, the rod portion 20 is detachably fixed to the main body portion 10. As a result, it is possible to replace the rod portion 20 with good reproducibility. It is possible to reduce work at the time of assembly and maintenance.

In the electron beam irradiation device 1, the partition between the cooling gas flow space 32 and the electron beam emission space R is performed by the wall member 24, and then, the nitrogen gas is ejected by the cooling gas ejection holes 40 formed in the wall member 24 to directly cool the electron beam emission window 11. It is possible to stably cool the electron beam emission window 11 even when the variation or deviation of the structure may occur due to assembly accuracy as compared to the structure in which the electron beam emission window 11 is directly cooled without providing the wall member 24 and the cooling gas ejection hole 40.

In the electron beam irradiation device 1, it has been found that there is a proportional relationship between the pressure of a nitrogen gas to be introduced into the rod portion 20 and the flow rate (l/min) of a nitrogen gas to be ejected from the cooling gas ejection hole 40. Therefore, the flow rate of the nitrogen gas to be ejected from the cooling gas ejection hole 40 can be controlled by suppressing the pressure of the nitrogen gas to be supplied from the nitrogen gas generator 37 to the rod portion 20 using the control unit 12 based on the proportional relationship.

Figure 7:
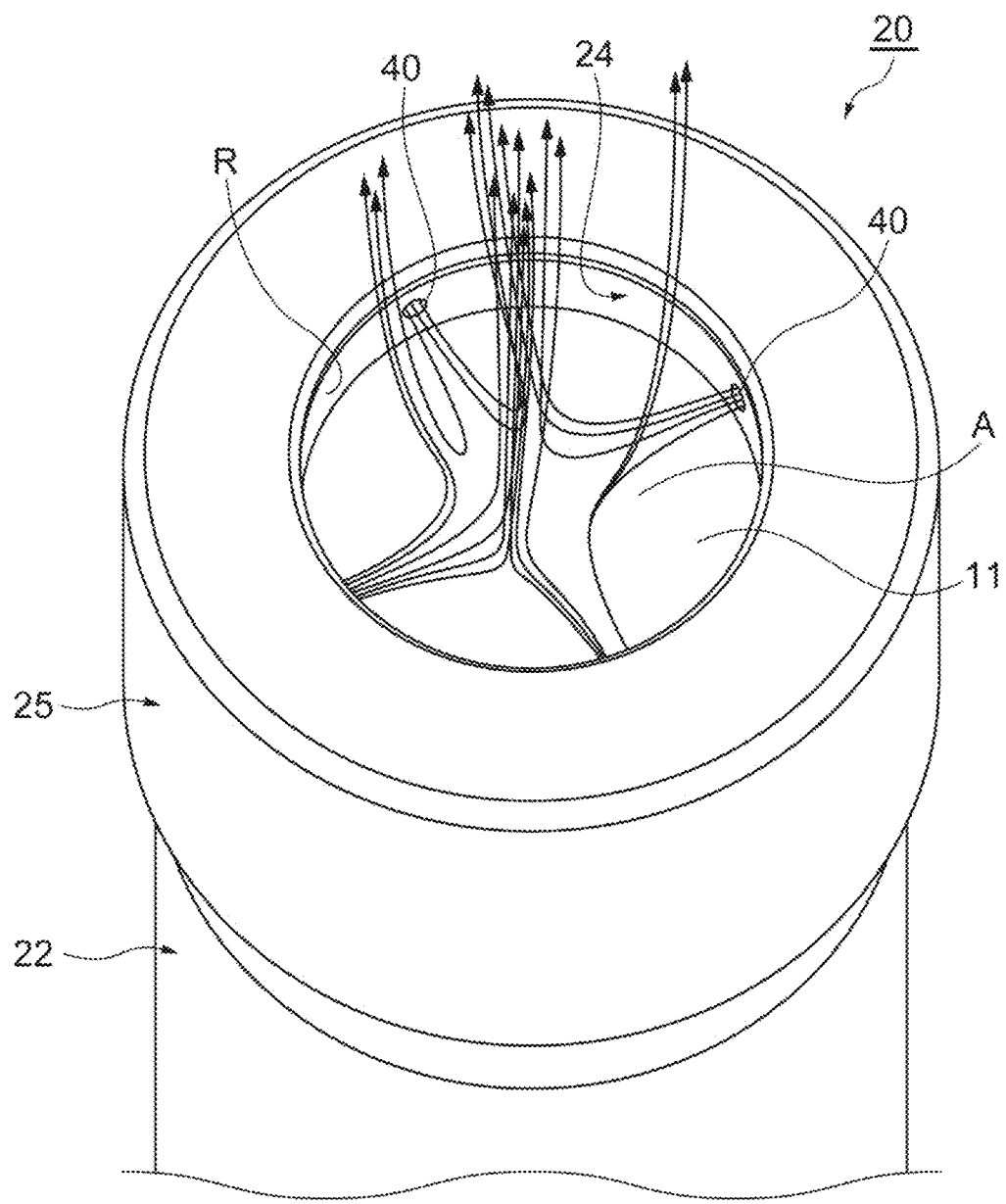
FIG. 7 is a view illustrating a result of analyzing flow of a nitrogen gas on the distal end side of the rod portion of FIG. 1.

FIG. 7 is a view illustrating a result of analyzing flow of a nitrogen gas on the distal end side of the rod portion 20 of FIG. 1. FIG. 7 is a perspective view of the electron beam emission side of the electron beam emission window 11. Arrows in the drawing are flow lines of nitrogen gases obtained by analysis. The nitrogen gases are blown from four directions toward the central portion (the electron beam emission region A) of the electron beam emission window 11 inside the electron beam emission space R. According to the analysis result illustrated in FIG. 7, it is possible to confirm that the nitrogen gas ejected from each cooling gas ejection hole 40 of the wall member 24 advances to spread toward the electron beam emission window 11, and hits the electron beam emission window 11 to change its direction toward the electron beam emission side (the upper side in the drawing) near the center of the electron beam emission window 11 and diffuse. It is possible to confirm that nitrogen gas can be brought into contact with the electron beam emission window 11 to cool the electron beam emission window 11.

Although the embodiment of the present invention has been described above, the present invention is not limited to the above-described embodiment, and may be modified and applied to other embodiments within a scope not changing a gist described in each claim.

In the above embodiment, the cooling gas ejection hole 40 has the circular cross section, but may have a cross-sectional shape other than the circular cross section and may have an elliptical cross-sectional shape. The cooling gas ejection hole 40 may be a slit having a rectangular cross section in order to enable cooling of a wide range. In addition, the cooling gas ejection holes 40 may be configured as follows, for example.

Figure 8:
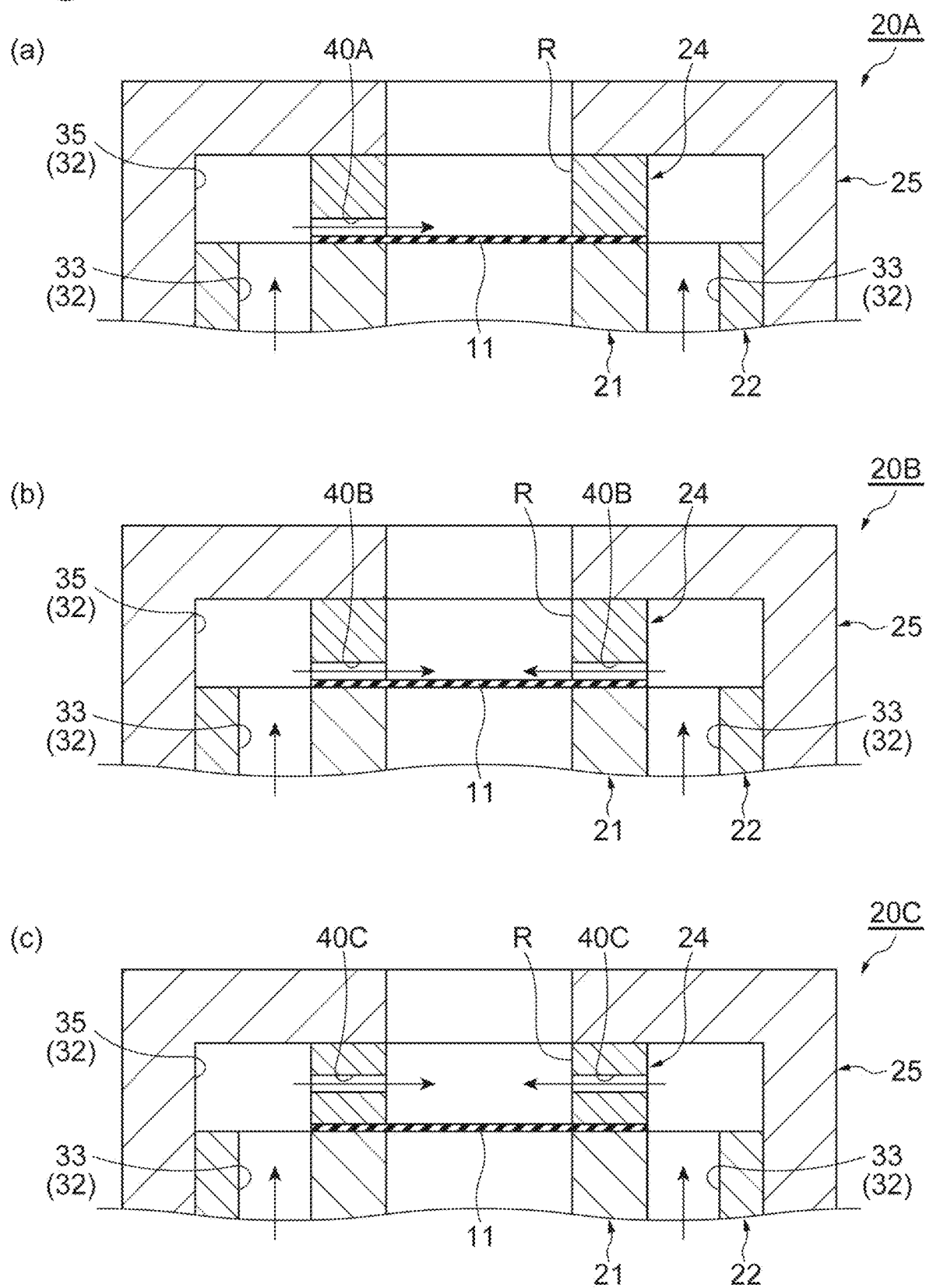
FIG. 8(*a*) is an enlarged cross-sectional view illustrating a distal end side of a rod portion according to a first modification.

FIG. 8(a) is an enlarged cross-sectional view illustrating a distal end side of a rod portion 20A according to a first modification. As illustrated in FIG. 8(a), the wall member 24 of the rod portion 20A is provided with a cooling gas ejection hole 40A that blows a nitrogen gas along a surface on the electron beam emission side of the electron beam emission window 11. The cooling gas ejection hole 40A is provided at the end portion on the proximal end side of the wall member 24. The cooling gas ejection hole 40A extends straight in the radial direction of the wall member 24. The cooling gas ejection hole 40A is not provided in a pair to face each other with a central axis of the wall member 24 interposed therebetween. According to the cooling gas ejection hole 40A, the nitrogen gas is brought into contact along the surface on the electron beam emission side of the electron beam emission window 11 so that heat of the electron beam emission window 11 can be efficiently carried, and the electron beam emission window 11 can be effectively cooled.

FIG. 8(b) is an enlarged cross-sectional view illustrating a distal end side of a rod portion 20B according to a second modification. As illustrated in FIG. 8(b), cooling gas ejection holes 40B similar to the cooling gas ejection hole 40A (see FIG. 8(a)) are formed in the wall member 24 of the rod portion 20B in a pair to face each other with a central axis of the wall member 24 interposed therebetween. Even in the cooling gas ejection hole 40B, a nitrogen gas is brought into contact along a surface on the electron beam emission side of the electron beam emission window 11 so that heat of the electron beam emission window 11 can be efficiently carried, and the electron beam emission window 11 can be effectively cooled.

FIG. 8(c) is an enlarged cross-sectional view illustrating a distal end side of a rod portion 20C according to a third modification. As illustrated in FIG. 8(c), the wall member 24 of the rod portion 30C is provided with a cooling gas ejection hole 40C that blows a nitrogen gas straightly along the radial direction into the electron beam emission space R. The cooling gas ejection hole 40C is provided in the central portion of the wall member 24 in the emission direction of the electron beam EB. The cooling gas ejection hole 40C extends straight along the radial direction of the wall member 24 and is not inclined to any of the distal end side and the proximal end side. The cooling gas ejection holes 40C are provided in a pair to face each other with a central axis of the wall member 24 interposed therebetween.

Although the above embodiment is configured such that the inner circumferential surface of the second tubular member 22 is in contact with the outer circumferential surface of the first tubular member 21 at the four points adjacent to the separating portion 21d in the cross section perpendicular to the extending direction of the rod portion 20, the inner circumferential surface of the second tubular member 22 may be in contact with the outer circumferential surface of the first tubular member 21 at three points, at two points, or at five points or more.

Figure 9:
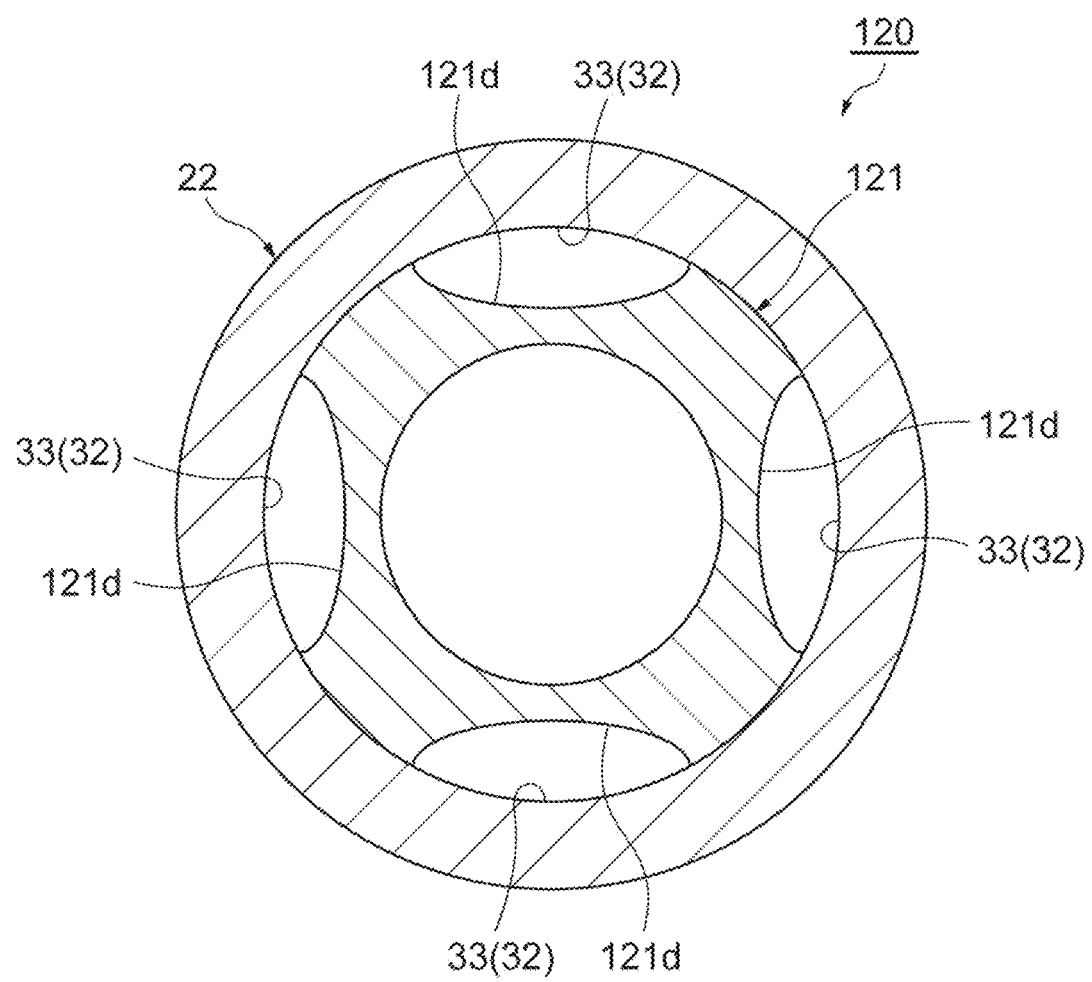
FIG. 9 is a cross-sectional view corresponding to a cross section taken along the line B-B of FIG. 3 of a rod portion according to a fourth modification.

In the above embodiment, the shape of the separating portion 21*d* is not particularly limited, and may be various shapes. For example, a separating portion 121*d* illustrated in FIG. 9 may be formed. The separating portion 121*d* is formed at four positions equally spaced in a circumferential direction on an outer circumferential surface of a first tubular member 121 of a rod portion 120. The separating portion 121*d* extends along an axial direction of the first tubular member 121. The separating portion 121*d* has a shape obtained by cutting out a part of the outer circumferential surface side of the first tubular member 121 with a curved surface that extends along the axial direction of the first tubular member 121 and is convex toward the inner side in the radial direction. A cross section perpendicular to an axial direction of the separating portion 121*d* has an elliptical shape with the radial direction as the short direction. Due to the above separating portion 121*d*, two pairs of curved surfaces, which have arcuate cross sections and face each other, are formed on the outer circumferential surface of the first tubular member 121. According to the separating portion 121*d*, the cooling gas flow path 33 can be widened while maintaining the thickness of the rod portion 120.

In the above embodiment, the number of the cooling gas ejection holes 40 may be one or plural. In the above embodiment, the number of the cooling gas flow paths 33 may be one or plural. In the above embodiment, the electron beam emission window 11 may be joined to the end portion on the distal end side of the first tubular member 21 by brazing or welding, for example. In the above embodiment, a length of the rod portion 20 is not particularly limited and may be any length as long as the length is set in accordance with a size or a shape of a container to be inserted.

The separating portion 21*d* is provided on the outer circumferential surface of the first tubular member 21 in the above embodiment, but in place of or in addition to such a configuration, a separating portion similar to the separating portion 21*d* may be provided on the inner circumferential surface of the second tubular member 22. In the above embodiment, it is sufficient for the separating portion to separate the outer circumferential surface of the first tubular member 21 and the inner circumferential surface of the second tubular member 22 so as to form the cooling gas flow path 33. The separating portion may be a notch extending along the extending direction of the rod portion 20, a groove extending along the extending direction of the rod portion 20, or a concave portion (concave path) extending along the extending direction of the rod portion 20.

In the above embodiment, the rod portion 20 (in particular, the first tubular member 21) may be extended toward the electron gun EG side, thereby forming the passing hole 10*a* through which the electron beam EB emitted from the electron gun EG passes. In this case, it is possible to easily obtain a central axis in an electron-passing route so that it is easy to adjust the electron beam EB. In addition, it is not necessary to form both the first tubular member 21 and the second tubular member 22 using the magnetic material. Both of the first tubular member 21 and the second tubular member 22 may be made of a nonmagnetic material, for example, stainless steel, aluminum, oxygen-free copper, or the like. In this case, the magnetic field formed by the adjusting electromagnetic coil 13 and the converging electromagnetic coil 14 can be easily guided to the electron beam EB in the first tubular member 21.

In the above embodiment, the adjusting electromagnetic coil 13 is used as the adjustment unit, but the adjustment unit is not particularly limited, and various types of means can be applied as the adjustment unit as long as the orbit of the electron beam EB can be adjusted. In the above embodiment, the converging electromagnetic coil 14 is used as the converging unit, but the converging unit is not particularly limited, and various types of means can be applied as the converging unit as long as the converging control of the electron beam EB is possible. In addition, there are cases where at least one of the adjustment unit and the converging unit is not provided. In addition, a plurality of the adjusting electromagnetic coils 13 and the converging electromagnetic coils 14 may be combined, and in this case, the electron beam EB can be controlled with high accuracy. In addition, the arrangement of the adjusting electromagnetic coil 13 and the converging electromagnetic coil 14 may be interchanged.

Figure 10:
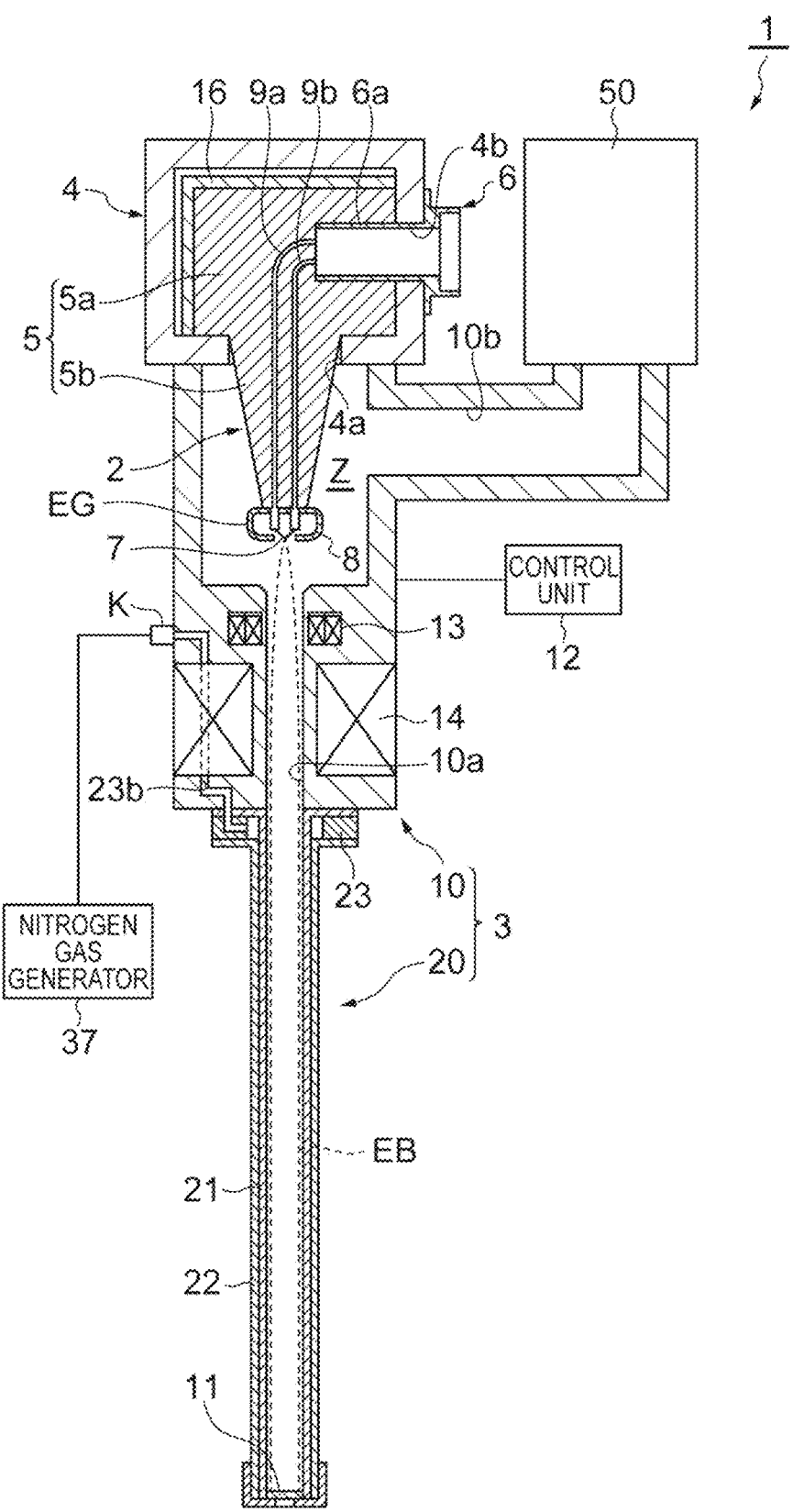
FIG. 10 is a cross-sectional view illustrating an electron beam irradiation device according to a fifth modification.

In the above embodiment, the gas introduction hole 23*a* (see FIG. 3) is formed to communicate the proximal end space 34 and the outside, but instead of this, a gas introduction hole 23*b* may be formed as illustrated in FIG. 10. The gas introduction hole 23*b* passes through the fixing member 23, the flange 21*a* of the first tubular member 21, and the main body portion 10. The nitrogen gas generator 37 is connected to the gas introduction hole 23*b* via the gas introduction portion K provided on an outer surface in the vicinity of an arrangement region of the adjusting electromagnetic coil 13 in the main body portion 10. As a result, a nitrogen gas generated by the nitrogen gas generator 37 is introduced into the proximal end space 34 from the gas introduction portion K via the gas introduction hole 23*b*. Since the gas introduction portion K is provided at a position separated from the rod portion 20 in this manner, the gas introduction portion K is less likely to obstruct insertion at the time of inserting the rod portion 20 into the bottle B, and it is possible to prevent the gas introduction portion K from deteriorating by being exposed to ozone or the like generated by the irradiation of the electron beam EB.

Incidentally, at least some of the embodiments and modifications described above may be arbitrarily combined. The above-described term "equal" includes not only the case of being exactly equal but also the case of being substantially equal. The above-described term "same" includes not only the case of being exactly the same but also the case of being substantially the same. The above-described terms "equal" and "same" include errors in terms of the design, measurement, or manufacture.

REFERENCE SIGNS LIST

1 electron beam irradiation device
2 electron beam generation unit
3 housing
10 main body portion
11 electron beam emission window
13 adjusting electromagnetic coil (adjustment unit)
14 converging electromagnetic coil (converging unit)
20, 20A, 20B, 20C, 120 rod portion
21, 121 first tubular member
21*d*, 121*d* separating portion
22 second tubular member
24 wall member
25 pressing member
32 cooling gas flow space
33 cooling gas flow path
34 proximal end space
35 distal end space
40 cooling gas ejection hole A electron beam emission region
EB electron beam
EG electron gun
R electron beam emission space

The invention claimed is:

1. An electron beam irradiation device comprising:
an electron gun configured to emit an electron beam;
a housing configured to have a main body portion housing the electron gun and a rod portion having a proximal end side connected to the main body portion and a distal end side protruding from the main body portion; and
an electron beam emission window provided on the distal end side of the rod portion,
wherein the rod portion includes:
a first tubular member having a tubular shape with an extending direction of the rod portion as an axial direction, is provided with the electron beam emission window at an end portion on the distal end side, and has an inside through which the electron beam passes;
a second tubular member having a tubular shape with the extending direction of the rod portion as an axial direction and surrounds the first tubular member;
a cooling gas flow space for a cooling gas introduced from the proximal end side to flow to the distal end side, and including at least a cooling gas flow path provided between an outer wall surface of the first tubular member and an inner wall surface of the second tubular member; and
a wall member provided so as to perform partition between an electron beam emission space facing an electron beam emission side of the electron beam emission window and the cooling gas flow space,
the wall member is provided with a cooling gas ejection hole that ejects the cooling gas from the cooling gas flow space to the electron beam emission space, and
the cooling gas ejection hole has a flow path sectional area smaller than a flow path sectional area of the cooling gas flow path.

2. The electron beam irradiation device according to claim 1, wherein
the cooling gas ejection hole ejects the cooling gas toward an electron beam emission region of the electron beam emission window.

3. The electron beam irradiation device according to claim 1, wherein
a plurality of the cooling gas ejection holes is provided in the wall member, and
the cooling gas flow space further includes a distal end space formed around the wall member and causing the cooling gas flow path to communicate with the plurality of cooling gas ejection holes.

4. The electron beam irradiation device according to claim 1, wherein
the cooling gas flow space includes a plurality of the cooling gas flow paths, and further includes a proximal end space which is formed on the proximal end side of the rod portion and communicates with the plurality of cooling gas flow paths, and into which the cooling gas is introduced from an outside the rod portion.

5. The electron beam irradiation device according to claim 1, wherein
at least one of the outer wall surface of the first tubular member and the inner wall surface of the second tubular member is formed with a separating portion separating the outer wall surface from the inner wall surface so as to form the cooling gas flow path, in a cross section perpendicular to the extending direction of the rod portion, and
the outer wall surface of the first tubular member and the inner wall surface of the second tubular member are in contact with each other at at least two points in the cross section perpendicular to the extending direction of the rod portion.

6. The electron beam irradiation device according to claim 5, wherein
the separating portion is formed on the outer wall surface of the first tubular member.

7. The electron beam irradiation device according to claim 1, further comprising:
an adjustment unit configured to adjust an orbit of the electron beam; and
a converging unit configured to control converging of the electron beam.

8. The electron beam irradiation device according to claim 1, wherein
at least one of the first tubular member and the second tubular member is made of a magnetic material.

9. The electron beam irradiation device according to claim 1, wherein
the electron beam emission window is arranged on an end face of the first tubular member on the distal end side, and
the wall member has a tubular shape and is arranged on a surface of the electron beam emission window on the electron beam emission side,
the electron beam irradiation device further comprising a pressing member detachably fixed to the second tubular member and configured to press the wall member toward the electron beam emission window.

* * * * *